(12) United States Patent
Flyash et al.

(10) Patent No.: US 9,011,419 B2
(45) Date of Patent: Apr. 21, 2015

(54) DISPOSABLE ELECTROMAGNETIC ENERGY APPLICATOR

(71) Applicants: Lion Flyash, Nazareth-Illit (IL); Boris Vaynberg, Zichron Yaakov (IL)

(72) Inventors: Lion Flyash, Nazareth-Illit (IL); Boris Vaynberg, Zichron Yaakov (IL)

(73) Assignee: Syneron Medical Ltd, Yokneam (IL)

( * ) Notice: Subject to any disclaimer, the term of this patent is extended or adjusted under 35 U.S.C. 154(b) by 0 days.

(21) Appl. No.: 14/146,547

(22) Filed: Jan. 2, 2014

(65) Prior Publication Data

US 2014/0171934 A1 Jun. 19, 2014

Related U.S. Application Data

(63) Continuation of application No. 13/427,884, filed on Mar. 23, 2012, now Pat. No. 8,641,703, which is a continuation of application No. 12/324,932, filed on Nov. 28, 2008, now Pat. No. 8,216,215.

(60) Provisional application No. 60/992,390, filed on Dec. 5, 2007.

(51) Int. Cl.
  *A61B 18/18* (2006.01)
  *A61B 18/14* (2006.01)
  *A61N 5/00* (2006.01)
  *A61B 18/20* (2006.01)
  *A61B 18/00* (2006.01)

(52) U.S. Cl.
  CPC ............ *A61B 18/18* (2013.01); *A61B 18/14* (2013.01); *A61N 5/00* (2013.01); *A61B 18/203* (2013.01); *A61B 2018/00011* (2013.01); *A61B 2018/00023* (2013.01); *A61B 2018/0016* (2013.01); *A61B 2018/00452* (2013.01); *A61B 2018/0047* (2013.01); *A61B 2018/00476* (2013.01); *A61B 2018/1467* (2013.01)

(58) Field of Classification Search
  USPC ................................ 606/9, 24, 33, 36, 37, 41
  See application file for complete search history.

(56) References Cited

U.S. PATENT DOCUMENTS

| | | | |
|---|---|---|---|
| 4,940,456 A | 7/1990 | Sibalis et al. |
| 5,087,240 A | 2/1992 | Sibalis |
| 5,158,537 A | 10/1992 | Haak et al. |
| 5,250,023 A | 10/1993 | Lee et al. |
| 5,445,609 A | 8/1995 | Lattin et al. |
| 5,445,611 A | 8/1995 | Eppstein et al. |
| 5,458,140 A | 10/1995 | Eppstein et al. |
| 5,498,235 A | 3/1996 | Flower |

(Continued)

FOREIGN PATENT DOCUMENTS

| | | |
|---|---|---|
| WO | WO-94/14062 | 6/1994 |
| WO | WO-96/17651 | 6/1996 |

(Continued)

*Primary Examiner* — Nicholas Lucchesi
*Assistant Examiner* — Diva K Chander
(74) *Attorney, Agent, or Firm* — Smith Risley Tempel Santos LLC; Gregory Scott Smith

(57) ABSTRACT

A skin treatment apparatus that includes, a disposable electrode carrier with a plurality of voltage-applying dome-shaped elements protruding from the surface of the electrode carrier. Further, the protruding elements are spaced apart in a pattern. The apparatus operates to apply a voltage to at least some of the protruding elements. The apparatus applies a voltage to the protruding elements with a magnitude that is sufficient to result in an electrical break down of the skin and thereby cause electric current enabling the desired treatment.

8 Claims, 13 Drawing Sheets

(56) References Cited

U.S. PATENT DOCUMENTS

| | | | |
|---|---|---|---|
| 5,674,191 A | 10/1997 | Edwards et al. | |
| 5,681,282 A * | 10/1997 | Eggers et al. | 604/114 |
| 5,698,217 A | 12/1997 | Wilking | |
| 5,722,397 A | 3/1998 | Eppstein | |
| 5,776,092 A | 7/1998 | Farin et al. | |
| 5,873,855 A * | 2/1999 | Eggers et al. | 604/114 |
| 5,885,211 A | 3/1999 | Eppstein et al. | |
| 5,888,198 A | 3/1999 | Eggers et al. | |
| 5,908,401 A | 6/1999 | Henley | |
| 5,961,482 A | 10/1999 | Chien et al. | |
| 5,983,130 A | 11/1999 | Phipps et al. | |
| 5,983,135 A | 11/1999 | Avrahami | |
| 6,022,316 A | 2/2000 | Eppstein et al. | |
| 6,024,733 A | 2/2000 | Eggers et al. | |
| 6,142,939 A | 11/2000 | Eppstein et al. | |
| 6,148,232 A | 11/2000 | Avrahami | |
| 6,173,202 B1 | 1/2001 | Eppstein | |
| 6,183,434 B1 | 2/2001 | Eppstein | |
| 6,275,728 B1 | 8/2001 | Venkatraman | |
| 6,302,874 B1 | 10/2001 | Zhang et al. | |
| 6,352,506 B1 | 3/2002 | Eppstein et al. | |
| 6,440,121 B1 * | 8/2002 | Weber et al. | 606/2 |
| 6,477,410 B1 | 11/2002 | Henley et al. | |
| 6,490,482 B2 | 12/2002 | Mori et al. | |
| 6,508,785 B1 | 1/2003 | Epp stein | |
| 6,510,341 B1 | 1/2003 | Kuribayashi et al. | |
| 6,527,716 B1 | 3/2003 | Eppstein | |
| 6,530,915 B1 | 3/2003 | Eppstein et al. | |
| 6,595,947 B1 | 7/2003 | Mikszta et al. | |
| 6,597,946 B2 | 7/2003 | Avrahami et al. | |
| 6,611,706 B2 | 8/2003 | Avrahami et al. | |
| 6,611,707 B1 | 8/2003 | Prausnitz et al. | |
| 6,615,079 B1 | 9/2003 | Avrahami | |
| 6,623,454 B1 | 9/2003 | Eggers et al. | |
| 6,632,193 B1 | 10/2003 | Davison et al. | |
| 6,678,554 B1 | 1/2004 | Sun et al. | |
| 6,692,456 B1 | 2/2004 | Eppstein et al. | |
| 6,708,060 B1 | 3/2004 | Avrahami et al. | |
| 6,711,435 B2 | 3/2004 | Avrahami | |
| 6,719,754 B2 * | 4/2004 | Underwood et al. | 606/32 |
| 6,743,211 B1 | 6/2004 | Prausnitz et al. | |
| 6,767,341 B2 | 7/2004 | Cho | |
| 6,773,431 B2 * | 8/2004 | Eggers et al. | 606/32 |
| 6,925,317 B1 | 8/2005 | Samuels et al. | |
| 7,062,317 B2 | 6/2006 | Avrahami et al. | |
| 7,123,957 B2 | 10/2006 | Avrahami | |
| 7,164,942 B2 | 1/2007 | A vrahami et al. | |
| 7,335,377 B2 | 2/2008 | Stern et al. | |
| 7,363,075 B2 | 4/2008 | Stern et al. | |
| 7,383,084 B2 | 6/2008 | Stern et al. | |
| 7,395,111 B2 | 7/2008 | Levin et al. | |
| 7,415,306 B2 | 8/2008 | Levin et al. | |
| 7,435,247 B2 * | 10/2008 | Woloszko et al. | 606/41 |
| 7,494,488 B2 * | 2/2009 | Weber | 606/2 |
| 7,558,625 B2 | 7/2009 | Levin et al. | |
| 7,643,874 B2 | 1/2010 | Nitzan et al. | |
| 2001/0051180 A1 | 12/2001 | Watanabe et al. | |
| 2002/0010412 A1 | 1/2002 | Eppstein | |
| 2002/0010414 A1 | 1/2002 | Coston et al. | |
| 2002/0082543 A1 | 6/2002 | Park et al. | |
| 2002/0091311 A1 | 7/2002 | Eppstein et al. | |
| 2002/0099308 A1 | 7/2002 | Eppstein et al. | |
| 2002/0161324 A1 | 10/2002 | Henley et al. | |
| 2002/0169394 A1 | 11/2002 | Eppstein et al. | |
| 2002/0193729 A1 | 12/2002 | Cormier et al. | |
| 2003/0078499 A1 | 4/2003 | Epp stein | |
| 2003/0092982 A1 | 5/2003 | Eppstein et al. | |
| 2004/0039342 A1 | 2/2004 | Eppstein et al. | |
| 2004/0039343 A1 | 2/2004 | Eppstein et al. | |
| 2004/0210214 A1 * | 10/2004 | Knowlton | 606/41 |
| 2005/0049543 A1 | 3/2005 | Anderson et al. | |
| 2005/0119605 A1 | 6/2005 | Sohn | |
| 2005/0203359 A1 | 9/2005 | Blank et al. | |
| 2007/0009542 A1 | 1/2007 | Levin et al. | |
| 2007/0031495 A1 | 2/2007 | Eppstein et al. | |
| 2007/0191827 A1 * | 8/2007 | Lischinsky et al. | 606/34 |
| 2007/0270732 A1 | 11/2007 | Levin et al. | |
| 2007/0287949 A1 | 12/2007 | Levin et al. | |
| 2007/0292445 A1 | 12/2007 | Levin | |
| 2008/0114281 A1 | 5/2008 | Birchall et al. | |
| 2008/0208107 A1 | 8/2008 | McRae et al. | |
| 2008/0214986 A1 | 9/2008 | Ivorra et al. | |
| 2008/0214988 A1 * | 9/2008 | Altshuler et al. | 604/21 |
| 2008/0274166 A1 | 11/2008 | Sacks et al. | |
| 2009/0105706 A1 * | 4/2009 | Livneh | 606/33 |
| 2009/0264810 A1 | 10/2009 | Eppstein et al. | |
| 2010/0174224 A1 | 7/2010 | Sohn | |
| 2010/0293807 A1 | 11/2010 | Bar-El et al. | |
| 2012/0022435 A1 | 1/2012 | Ignon et al. | |
| 2012/0022504 A1 | 1/2012 | Epshtein et al. | |

FOREIGN PATENT DOCUMENTS

| | | |
|---|---|---|
| WO | WO-96/40364 | 12/1996 |
| WO | WO-97/07734 | 3/1997 |
| WO | WO-97/16222 | 5/1997 |
| WO | WO-98/00193 | 1/1998 |
| WO | WO-98/29134 | 7/1998 |
| WO | WO-99/44507 | 9/1999 |
| WO | WO-99/44508 | 9/1999 |
| WO | WO-99/44637 | 9/1999 |
| WO | WO-99/44638 | 9/1999 |
| WO | WO-99/44678 | 9/1999 |
| WO | WO-00/03758 | 1/2000 |
| WO | WO-00/04832 | 2/2000 |
| WO | WO-00/15102 | 3/2000 |
| WO | WO-00/59371 | 10/2000 |
| WO | WO-00/74583 | 12/2000 |
| WO | WO-00/74767 | 12/2000 |
| WO | WO-00/76575 | 12/2000 |
| WO | WO-01/35820 | 5/2001 |
| WO | WO-02/090210 | 11/2002 |
| WO | WO-03/039620 | 5/2003 |
| WO | WO-03/077970 | 9/2003 |
| WO | WO-03/077971 | 9/2003 |
| WO | WO-03/101507 | 12/2003 |
| WO | WO-2006/131931 | 12/2006 |
| WO | WO-2006/131931 A2 | 12/2006 |
| WO | WO-2008/091878 | 7/2008 |
| WO | WO-2009/047774 | 4/2009 |

\* cited by examiner

DISPOSABLE ELECTROMAGNETIC ENERGY APPLICATOR

CROSS-REFERENCE TO RELATED APPLICATIONS

This application is being filed in the United States Patent Office under 35 USC 111 and 37 CFR 1.53(b) as a continuation application of the patent application that was filed in the United States Patent Office on Mar. 23, 2012 and assigned Ser. No. 13/427,884, which application is a continuation application of the patent application that was filed in the United States Patent Office on Nov. 28, 2008 and assigned Ser. No. 12/324,932, which application claims the benefit of the priority date of the U.S. Provisional Application for patent that was filed on Dec. 5, 2007 and assigned Ser. No. 60/992,390, each of these applications are hereby incorporated by reference.

BACKGROUND

The present device is related to the field of skin treatment and, in particularly, skin treatment by electromagnetic energy for dermatological and cosmetic purposes.

Skin tightening or wrinkles reduction, removal of skin lesions and reduction of subcutaneous fat layers, or adipose tissue, is a dermatological and aesthetic treatment for which there is a growing demand. Among the different physical therapies available, the application of radio frequency is emerging as a leading technology for use in the removal of skin wrinkles and for performing other body shaping procedures. Methods associated with this technology are typically based on the delivery of a dose of electromagnetic energy to a target section or volume of the skin of a recipient and into the deeper subcutaneous skin layers to a volume of tissue to be treated. This energy shrinks or destroys collagen that is contained in the skin and tightens the skin. Typically, the energy is delivered by an applicator being in contact with the section of the skin to be treated and driven by a source of suitable electromagnetic energy, and particularly RF energy.

The electromagnetic energy is typically delivered to a target section of the skin of the recipient by selecting a contact element that is compatible with the treated section size. Alternatively, a plurality of contact elements can be utilized, in which the plurality of elements contact and penetrate discrete points of the target section of the skin. In the later case, the healing period is typically shorter. Although both modes of treatment are effective, the use of multiple contact elements treating discrete points of a target section more effectively tightens the skin, reduces wrinkles, and improves the skin appearance.

Currently, the applicators that deliver electromagnetic energy to the target section of the skin and induce the electric current therein are designed for multiple treatments. The proper operation of these applicators mandates introduction of an electrically conductive fluid or gel that is applied between the electrodes or contact elements and the target section of the skin. These conductive fluids generally have a resistance level that is higher than the resistance of the upper skin layer stratum corneum and they facilitate the application or conduction of electric current to the skin and tissue. The introduction of this electrically conductive fluid or gel between the electrodes and the treated section of the skin complicates the treatment process in that it requires the applicator to be cleaned prior to its next use. Such cleaning procedures typically require certain sterilization-like operations to be applied to the applicator prior to using the applicator on the next patient. Although the use of disposable applicators is known in the art, these disposable applicators are expensive elements and as such, have not been widely use in the industry. In addition, these disposable applicators also require the use of an electrically conductive fluid or gel being applied between the electrodes or contact elements and the treated section of the skin.

Some of the applicators that avoid the need for an electrically conductive fluid or gel in skin treatment include skin penetrating electrodes. When using these skin penetrating electrodes, the tending party is required to apply a sufficient amount of pressure to the applicator so as to ensure that the electrodes actually do penetrate the skin. The penetrating electrodes usually have sharp tips, require care in handling, and post treatment electrode processing or disposal.

Therefore, there is a need in the industry for a non-invasive or non-penetrating method of skin treatment and an applicator that can operate on dry skin, without conductive fluid having to be applied between the skin and the applicator. There is a further need in the art for a disposable applicator, or at least an applicator that includes disposable parts for electromagnetic radiation skin treatment. There is also a need in the art for a disposable applicator that penetrates the skin without involving sharp mechanical elements and producing similar treatment results. There is also a need in the art for an applicator that is capable of affecting a relatively large skin area without creating a need to leave treatment patches on the skin area. These and other needs in the art are met by the various embodiments that are described within this document.

BRIEF SUMMARY

One embodiment of the present apparatus is directed towards meeting the various needs in the art by providing a skin treatment apparatus that includes, but is not limited to, a disposable, electrode carrier with a plurality of voltage-applying dome-shaped elements protruding from the surface of the electrode carrier. Further, in some embodiments, the protruding elements are spaced apart in a pattern. The apparatus in this embodiment of the invention operates to apply a voltage to at least some of the protruding elements. The apparatus applies a voltage to the protruding elements with a magnitude that is sufficient to result in an electrical break down of the skin and thereby cause electric current enabling the desired treatment.

BRIEF DESCRIPTION OF THE SEVERAL VIEWS OF THE DRAWING

Various embodiments of the present apparatus, including method and apparatus embodiments, are disclosed are herein presented, by way of non-limiting examples only, with reference to the accompanying drawings, wherein like numerals depict the same elements throughout the text of the specifications.

FIG. 6A is a side view of the assembly and FIG. 6B is a top perspective view looking in the direction of arrow B.

FIG. 8A illustrates a three-dimensional carrier having a cylindrical shape. FIG. 8B illustrates a three-dimensional carrier having a triangular prism shape.

FIG. 9A illustrates an applicator consisting of a handle having connection to a cooling fluid supply. FIG. 9B illustrates an applicator utilizing the disposable carrier of FIG. 8C.

DETAILED DESCRIPTION OF EXEMPLARY EMBODIMENTS

Figure 1A:
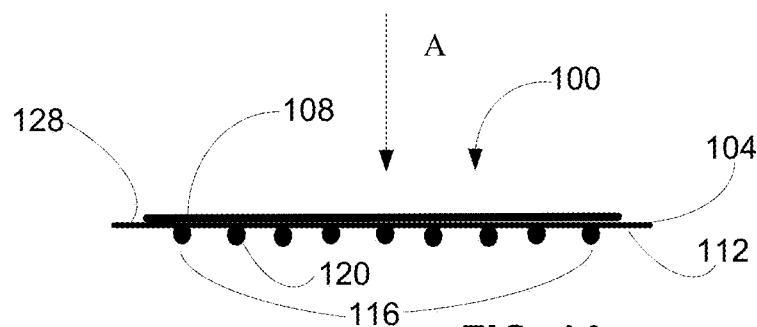
FIG. 1A is a profile diagram of a disposable flexible carrier embodiment of the present apparatus including an array of elements for contacting and sourcing voltage to a target section of skin.

FIG. 1A is a profile diagram of an embodiment of a disposable flexible carrier including an array of elements for contacting and sourcing voltage to a target section of skin.

In the exemplary embodiment illustrated in FIG. 1A, a carrier 100 is produced by attaching a flexible substrate 104 to another flexible substrate or backing 108 made of a similar material as substrate 104, or other suitable insulating material. Substrate 104 may be made of a variety of material, and a non-limiting example of a suitable material includes polyimide film or similar material, with a thickness of 0.5 mil to 6 mil (12.5 micron to 150 micron). The substrate 104 has on one or first of its sides/surfaces 112 an array or matrix of miniature (microscopic), discrete, voltage to skin application elements 116 protruding from surface 112 and terminated by dome type shapes 120.

Figure 1B:
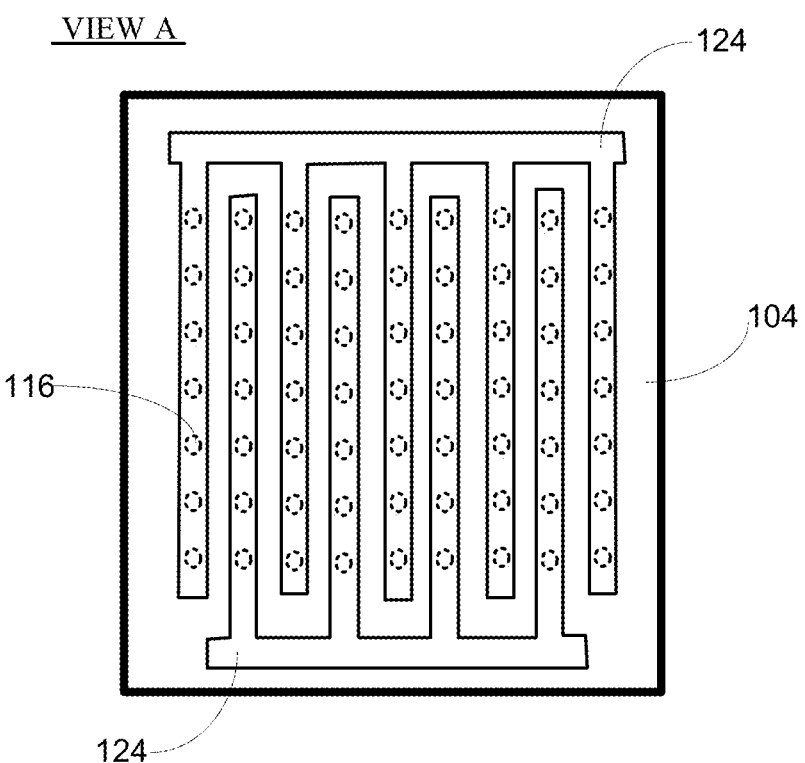
FIG. 1B is a planar view of an exemplary layout for conductors and contacting elements for a disposable carrier such as those illustrated in FIG. 1A and FIG. 1C.
Figure 1C:
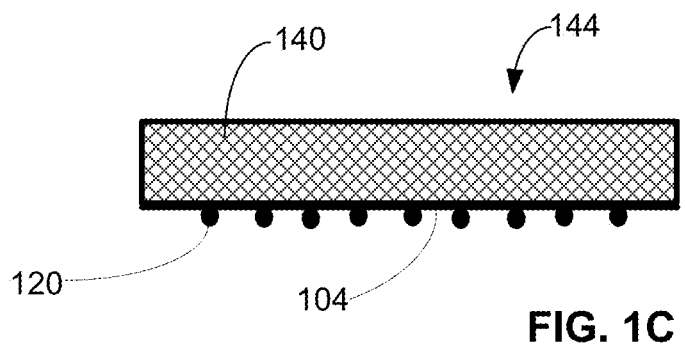
FIG. 1C is a profile diagram of a disposable rigid carrier embodiment of the present apparatus including an array of elements for contacting and sourcing voltage to a target section of skin.

FIG. 1B is a planar view of an exemplary layout for conductors and contacting elements for a disposable carrier such as those illustrated in FIG. 1A and FIG. 1C. A pattern of conductors 124 is illustrated on one side of the substrate 104. The pattern of conductors 124 enables addressing of the entire array of conductive elements 116, a group of the array of conductive elements 116, or each of the conductive elements 116 individually. Electric contact with a source of RF voltage (not shown) is produced on a second side 128 of the substrate 104. Carrier 100 is configured to allow quick attachment to an applicator. The term "carrier" in the context of the present disclosure means a substrate having an array of voltage to skin application elements, a two dimensional array or matrix of voltage to skin application elements, and as will be demonstrated below a three-dimensional shape substrate having on its external surface voltage to skin application elements.

FIG. 1C is a profile diagram of an embodiment of a disposable rigid carrier including an array of elements for contacting and sourcing voltage to a target section of skin. In this exemplary embodiment, the flexible substrate 104, similar to the embodiment illustrated in FIG. 1A, includes an array of voltage to skin application elements 116 and a pattern of conductors 124 exist on one side of the substrate 104. However, a stiffener or rigid backing 140, typically made of a rigid material with sufficient thickness such as a glass-epoxy or similar insulating material is attached to the other side of substrate 104. This structure forms a rigid carrier 144. In this embodiment, the carrier 144 can be easily attached to a applicator (not shown) through a variety of manners. For instance, mounting holes can be drilled through the carrier 144 material, bayonet type pins can be attached to the carrier 144 material, or other quick mounting arrangements can be utilized. Such arrangements enable a quick attachment and release of the carrier 144 to the applicator. An arrangement of contacts enabling connection to a source of radio frequency voltage is provided by forming on the carrier 144 contact points or strips communicating with respective contact arrangements made in substrate 104.

Figure 2A:
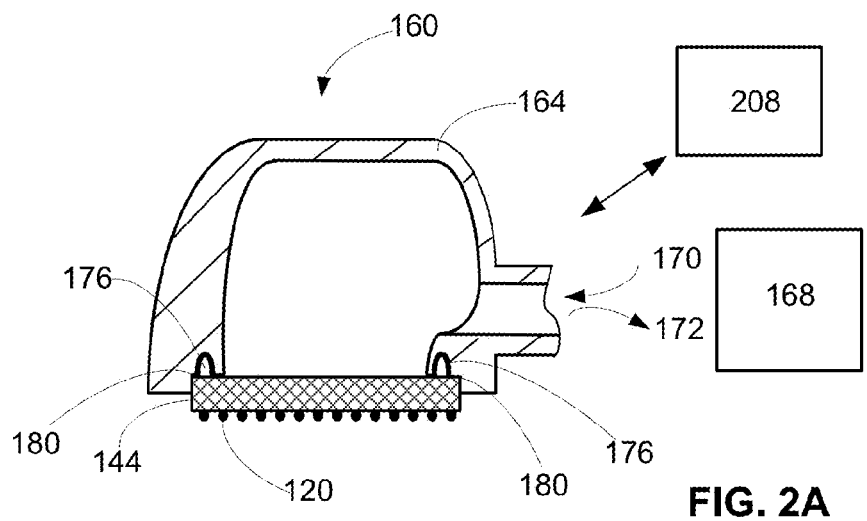
FIG. 2A is a cross sectional view of an exemplary embodiment of an applicator suitable for mounting of the disposable carriers 144, which houses voltage to skin application elements 116.

FIG. 2A is a cross sectional view of an exemplary embodiment of an applicator suitable for mounting of the disposable carriers 144, which houses voltage to skin application elements 116. FIG. 2A illustrates an applicator 160 that comprises a hand piece 164 with suitable connection to a source of RF voltage source 208 and if necessary, to a source of cooling fluid 168. In the context of the present disclosure, the term fluid includes liquid and gas. Arrows 170 and 172 illustrate cooling fluid into and out of the applicator 160 flow. The cooling fluid may flow into the applicator 160 during use and then be drained or, a continuous flow of cooling material may cycle through the applicator 160 by including an in and out tube or chamber in the applicator 160. In the embodiment illustrated in FIG. 2A, the carrier 144 is inserted into the hand piece 164, guided by bayonet pins 176 or by any other type of connection allowing fast assembly and removal of the carrier 144 from the hand piece 164. Contacts for conducting electromagnetic energy, such as RF energy, into the carrier 144 may be formed at the point where the surface of the carrier 144 meets the surface of the applicator 160. Alternatively, the bayonet pins 176 may serve as the electrical contact.

RF energy may be provided to the carrier 144 by applying RF voltage generated by RF voltage source 208 to the contacts. RF voltage source 208 may provide RF voltage to dome shaped elements 120 in a mode where individual dome shaped elements 120 are operated, all of the dome shaped elements 120 operate simultaneously, some of the elements are addressed in a random sequence.

Figure 2B:
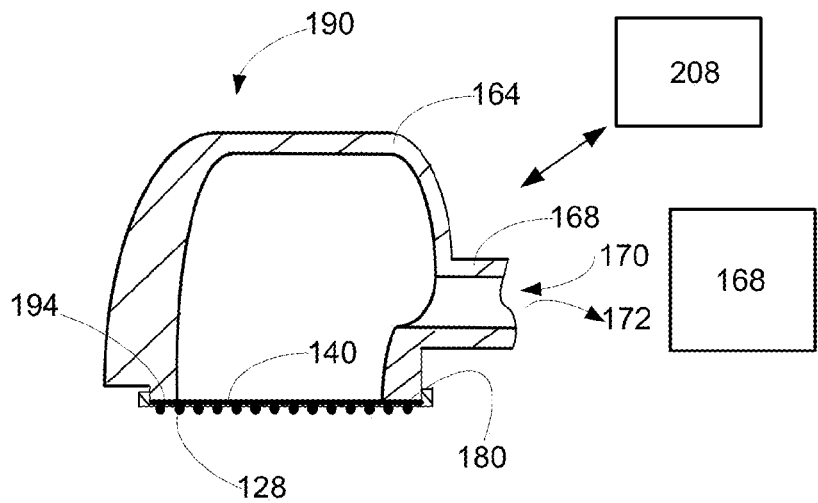
FIG. 2B is a cross sectional view of an exemplary embodiment of an applicator suitable for mounting of the disposable carrier, which houses voltage to skin application elements.

FIG. 2B is a cross sectional view of an exemplary embodiment of an applicator suitable for mounting of the disposable carrier 100, which houses voltage to skin application elements 116. FIG. 2B illustrates an applicator 190 that comprises a hand piece 164 with suitable connection to a source of RF voltage source 208 and if necessary, to a source of cooling fluid 168. In FIG. 2B, the applicator 190 is joined or connected to the disposable flexible carrier 100. A snap-on frame 194 attaches carrier 140 to the hand piece 164. Contacts for conducting electromagnetic energy may be formed in a similar way at junctions 180, provided that the rear surface 140 of flexible carrier 100 has a mating contact strip.

In an additional embodiment (not shown), the applicators 160 and/or 190, or similar applicators, may be configured to operate without cooling liquid being applied.

Figure 2C:
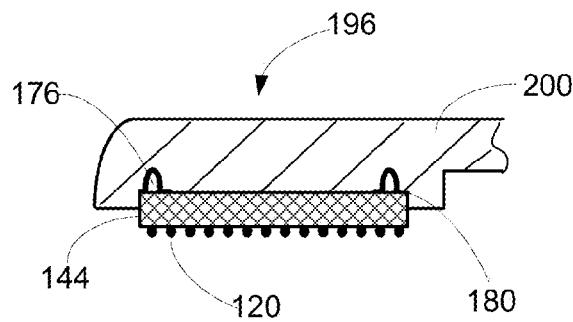
FIG. 2C is a cross-sectional view of another exemplary embodiment of an applicator suitable for mounting of a disposable carrier.

FIG. 2C is a cross-sectional view of another exemplary embodiment of an applicator suitable for mounting of a disposable carrier. In the illustrated embodiment, the rigid disposable carrier 144 illustrated in FIG. 1C is shown as being attached or coupled to an applicator 196 which does not include the hollow core defined by the applicator hand piece 200 as does the embodiments illustrated in FIGS. 2A and 2B. The illustrated embodiment of the applicator 196 precludes the use of a cooling liquid. It should be appreciated that the embodiment illustrated in FIG. 2C may also be used with a carrier as illustrated in FIG. 1A or other carrier structure.

The exemplary disposable carriers 100 and 144 may be used for purposes, such as dermatological or cosmetic skin treatment. As used herein, the term "skin treatment" includes treatment of various skin layers such as stratum corneum, dermis, epidermis, skin rejuvenation procedures, pigmented lesions removal, and such procedures as collagen shrinking or destruction.

Figure 3A:
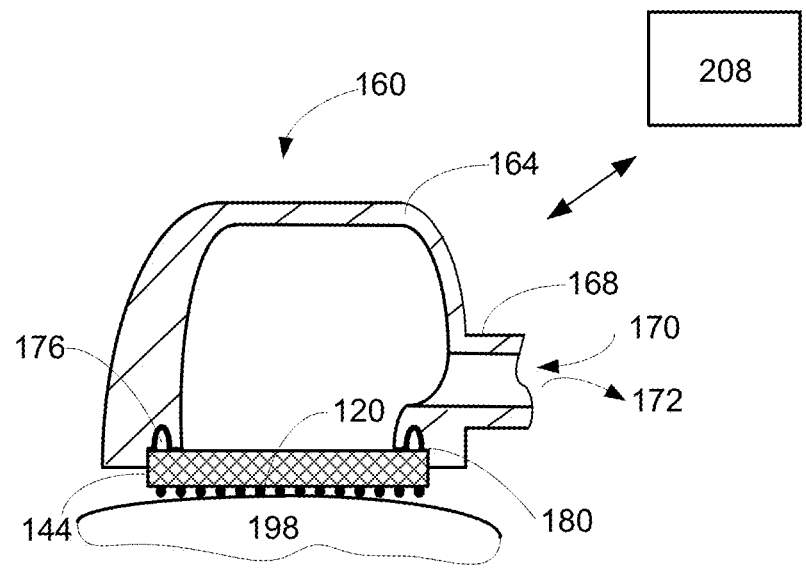
FIG. 3A is an environmental diagram illustrating the exemplary embodiment of the applicator and carrier of FIG. 2A being used on a target.
Figure 3B:
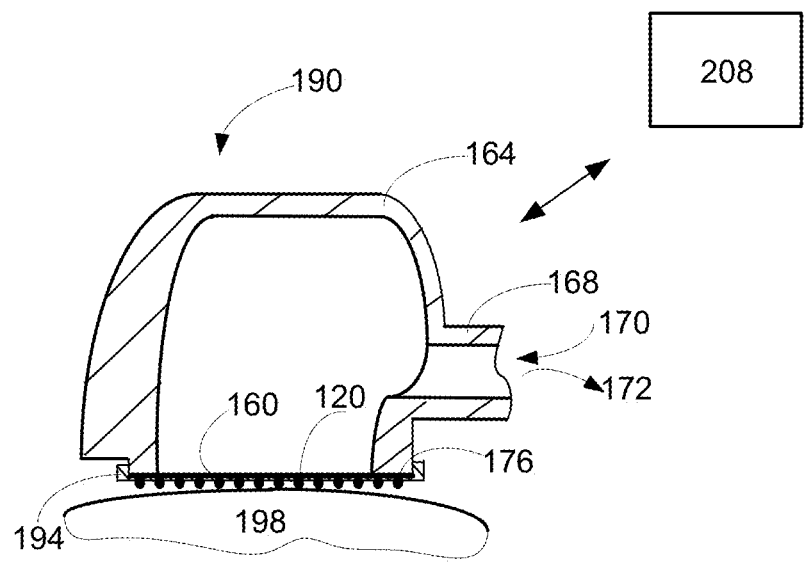
FIG. 3B is an environmental diagram illustrating the exemplary embodiment of the applicator and carrier of FIG. 2B being used on a target.

FIG. 3A is an environmental diagram illustrating the exemplary embodiment of the applicator and carrier of FIG. 2A being used on a target. FIG. 3B is an environmental diagram illustrating the exemplary embodiment of the applicator and carrier of FIG. 2B being used on a target. In the illustrated environments, a target is shown as being treated by an applicator 160 or 190 containing a plurality of spaced apart voltage applying elements 116 terminated by dome shaped ends 120 being applied to a target section of skin 198 such that elements 116 (FIG. 1B) terminated by domes 120 contact skin 198 surface. Because of the structure of the array of contact elements 116, the contact elements can be applied at a plurality of discrete and separate locations in the target section of skin 198. When the contact elements 116 are in place, a temporary, momentary, transient or even a steady voltage can be communicated between the contact elements 116 and a source of RF voltage 208—when enabled. The source 208 begins supplying contact elements 116 terminated by domes 120 with a voltage and gradually increases the supplied voltage value. It is well known that stratum corneum, the upper skin layer, is a dielectric and until certain voltage stressing it beyond its dielectric strength is applied to it, the stratum corneum resists electrical breakdown. As the RF voltage supplied by source 208 exceeds the electrical breakdown threshold, an electrical discharge takes place. The absence of a conductive fluid between the skin and the electrodes of the applicator 160 or 190 allows the device to achieve of a higher skin break-down potential and prevents the occurrence of a short circuit between the individual voltage supplying elements 116. The absence of a conductive fluid also facilitates limiting fractional skin damage caused by the RF voltage or energy radiating from the domes 120 to the skin contact points only. The discharge ablates the stratum corneum and since the coupling between voltage supplying elements 116 terminated by domes 120 and the skin is a conductive coupling, it enables electric current flow from the apex of dome 120 to highly conductive epidermis and dermis and deeper located skin layers. Enabled by skin breakdown, electric current heats and coagulates some of the target section of skin 198 volume initially in contact with the domes 120 and in immediate vicinity of domes 120 generating an array or matrix of microscopic skin wounds. The dome shaped form 120 of the voltage applying elements 116 facilitates electric discharge that takes place between the apex of the dome 120 and contact spot on the skin. The domes 120 however, do not penetrate the skin. Healing of these wounds tightens the damaged section 212 (see FIG. 4B) of the target section of skin 198 and reduces or removes wrinkles existing at this skin section.

Figure 4A:
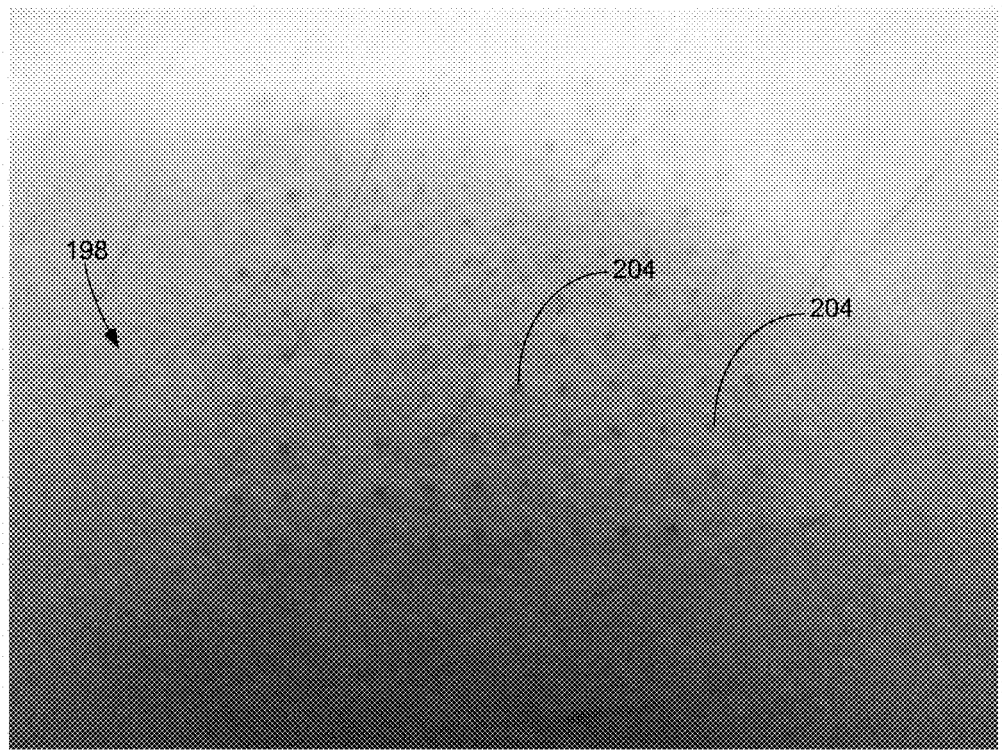
FIG. 4A is an image of a target section of skin showing an affected/treated section of skin 212 within the target section of skin and illustrating micro wounds.
Figure 4B:
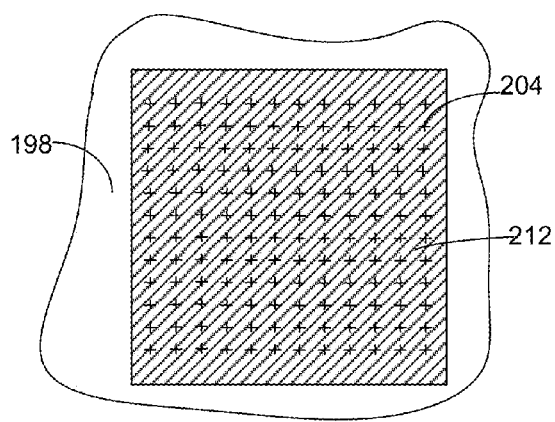
FIG. 4B is a graphical representation of a treated section of skin within the target section of skin with crosses indicating the location of micro wounds.

FIG. 4A is an image of a target section of skin 198 showing an affected/treated section of skin 212 within the target section of skin 198 and illustrating micro wounds 204. FIG. 4B is a graphical representation of a treated section of skin 212 within the target section of skin 198 with crosses indicating the location of micro wounds 204.

Figure 5:
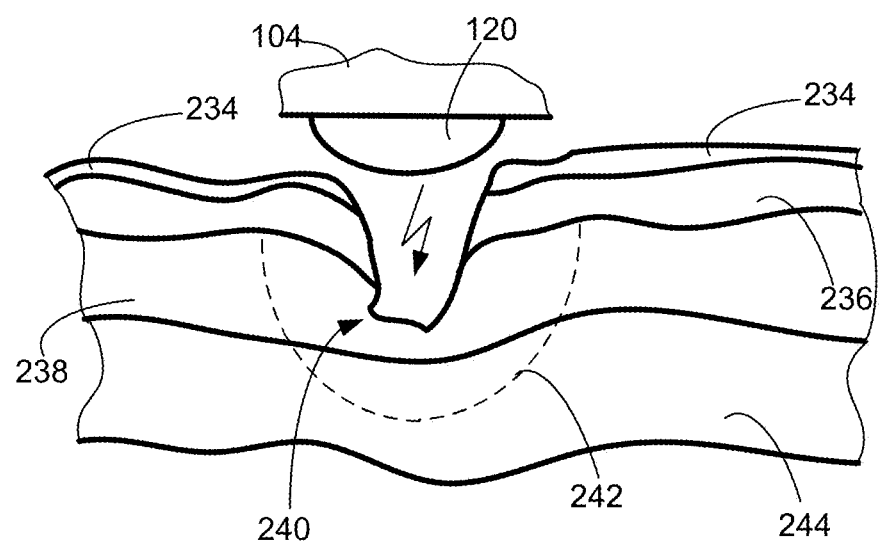
FIG. 5 is a schematic illustration of a cross section of a micro wound.

FIG. 5 is a schematic illustration of a cross section of a micro wound. It shows the area ablated by electrical discharge, represented as an arrow emanating from the apex of electrode dome 120, stratum corneum 234. The discharge has further penetrated the epidermis 236 and to some extent, the dermis 238 as well. An even deeper skin layer is deformed into a crater like structure 240 with coagulated walls. The phantom lines 242 are provided to illustrate the temperature distribution profile induced by the electric current. A maximal temperature is shown as existing at the center of the crater. The increase of temperature includes a certain depth of adipose tissue 244. When the temperature rises above a certain value, it operates to shrink and destroys the collagen fibers. Shrinking of the collagen fibers has the effect of tightening the skin and reducing wrinkles.

The size of the substrate on which the array of contact elements 116 (FIG. 1B) terminated by domes 120 are mounted determines the size of the affected skin surface 212 (The affected skin surface generally has a reddish color after treatment). Current sizes of substrates bearing the voltage applying elements range from 5×5 mm2 to 25×25 mm2. The array of elements 116 may be located on the surface of the substrate 104 or similar substrate as an evenly or randomly spaced matrix of for example, 12×12 electrodes, 16×16 electrodes, 16×24 electrodes, or any other number and configuration of the electrodes. With regards to the various embodiments, the term randomly is intended to include true randomness, as well as pseudo randomness or even predictive sequencing with a variety of lengths of sequences. In some embodiments, the domes 120 may be located in a form adapted to treat certain irregular shape skin area. Only the apex of the domes 120 is in contact with target section of the skin 198. The diameter of this contact area is about 10 to 20 micron. Accordingly, the damaged skin surface in relation to the affected (red) skin surface is a ratio of about $1:10^{-6}$ More specifically, this ratio reflects the area of the target section of skin being treated that is damaged by application of the RF voltage (i.e., the spark) and the target section of skin—which is left with a reddish color after treatment due to the irritation of the skin. The affected skin surface is generally equal to the size of the substrate on which domes 120 are mounted. For treatment of the next target section of skin, the applicator is moved (translated) over the skin in a patch like step motion and applied to the next target section of skin to be treated. This has a tendency to slow down the treatment process and requires multiple treatment sessions. In addition, this type of treatment leaves the skin a with a clearly visible patchy pattern of treated and untreated skin sections. In general, it can take a considerable amount of time before the pattern becomes less pronounced.

Because the damaged skin surface is extremely small, there may be no need for cooling the applicator unit and thus, almost all treatments may be performed with an applicator that does not need special cooling means.

Depending on the intensity of the voltage applied, the electric current developed, and the duration of the application to skin, the current that is enabled or delivered as a result of the breaking down of the discharged skin may be enhanced and maintained for a time sufficient for the collagen tissue shrinkage or destruction. This further facilitates process of tightening the target section of skin 198. Typical the duration of the application of the RF voltage to the skin would be in the range of 10 microseconds to 200 millisecond and the voltage values would be in the range of 10 volts to 1000 volts.

It should be understood that treatment applied with the above-described applicators by itself is a non-invasive treatment. The domes 120 of the array of contact elements 116 do not penetrate the skin being treated. Upon completion of the patient skin treatment, the carriers 100 or 144 used to apply or distribute the voltage to the target section of skin may be removed from applicators 160 and 190 (FIGS. 2A and 2B) and disposed of. It should also be noted that the carriers 100 or 144, although disposable upon completion of the treatment, are also suitable for a number of treatments and may be used for repeat treatments of the same patient.

Figure 6A:
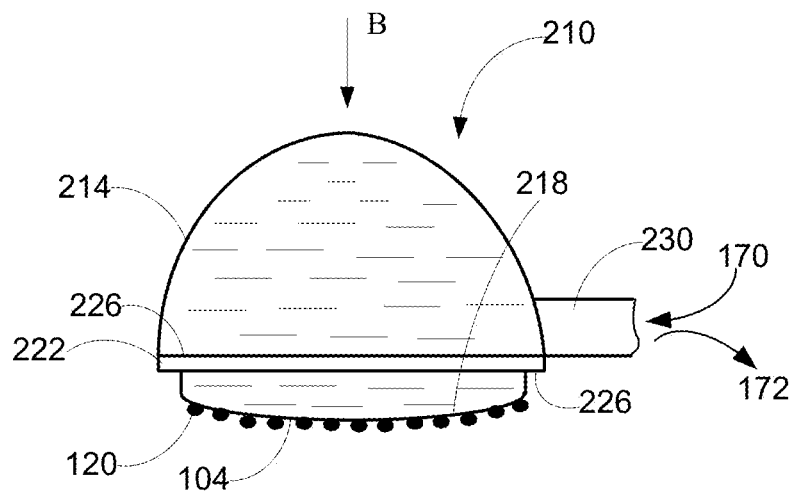
FIGS. 6A and 6B are schematic diagrams illustrating a third exemplary embodiment of a disposable flexible voltage-to-skin application elements carrier combined with a cooling facility for treatment of a plurality of discrete and separate skin volumes.
Figure 6B:
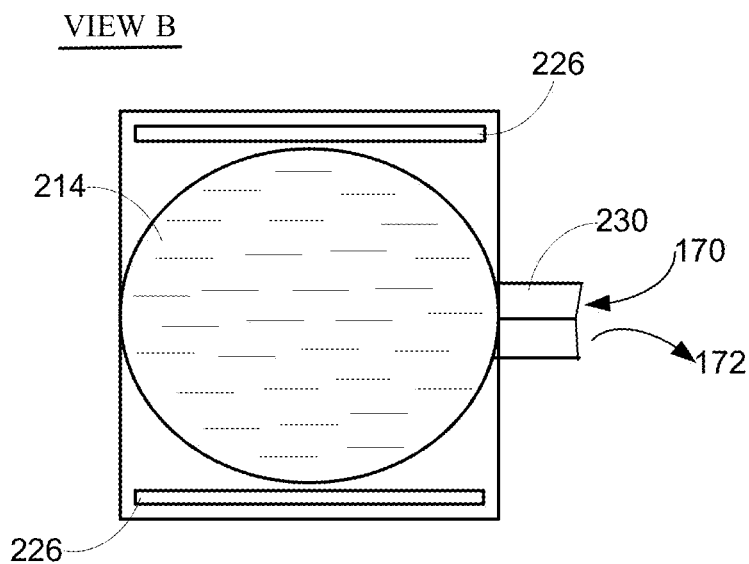

FIGS. 6A and 6B are schematic diagrams illustrating a third exemplary embodiment of a disposable flexible voltage-to-skin application elements carrier combined with a cooling facility for treatment of a plurality of discrete and separate skin volumes. FIG. 6A is a side view of the assembly and FIG. 6B is a top perspective view looking in the direction of arrow B. Assembly 210 includes a cooling facility, which is a hollow fluid reservoir 214 having at least one flexible wall 218. In one embodiment, the flexible substrate 104 which holds the voltage-to-skin application elements is laminated to the flexible wall 218. In this configuration, the flexible wall 218 replaces the flexible substrate 108. In an alternative embodiment, flexible carrier 100 is used as a wall of reservoir 214. Other cooling means, for example a thermo-cooler, heat pipe or similar may be used instead of fluid. Reservoir 214 includes a relatively rigid section 222 that bears contact strips 226 for conducting energy to flexible carrier 100. Generally, contact strips may be deposited in any location including the external part of the reservoir wall as long as they enable good electrical contact with the RF voltage source. Reservoir 214 includes a fluid input and output connection 230 and electrical connection (not shown) to a source of RF voltage. The cooling fluid may be water or some other suitable fluids.

Figure 7A:
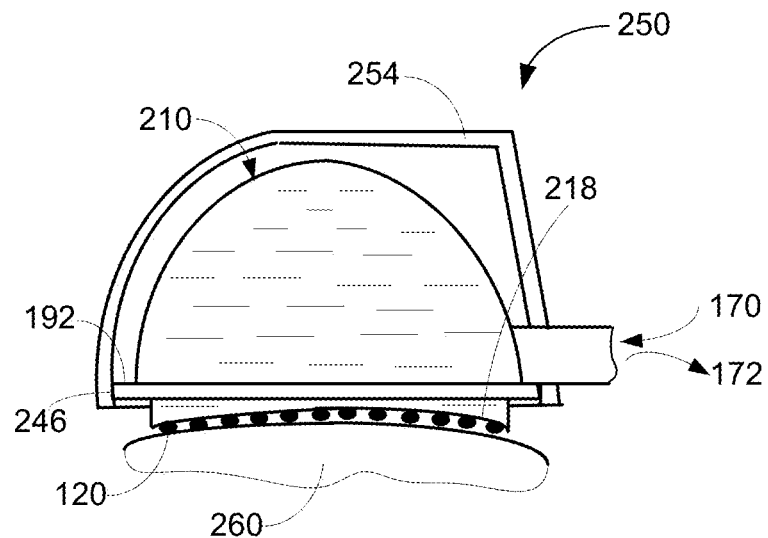
FIGS. 7A and 7B are different views of environmental drawings illustrating the use of the applicator containing assembly of FIGS. 6A and 6B.
Figure 7B:
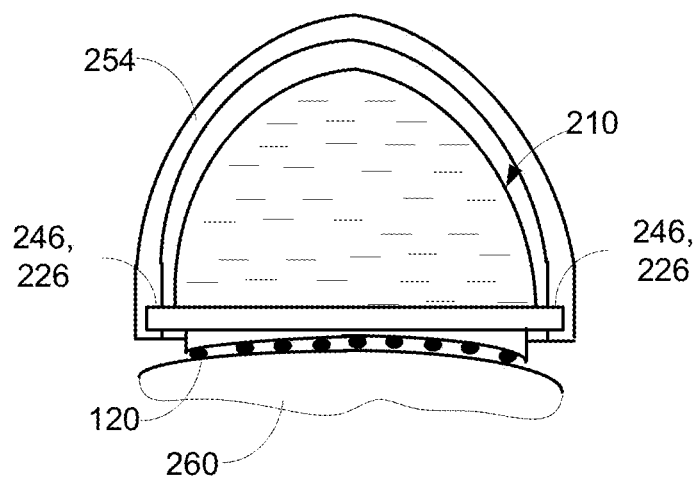

FIGS. 7A and 7B are different views of environmental drawings illustrating the use of the applicator containing assembly 210 of FIGS. 6A and 6B. The applicator 250 comprises a hand piece 254 with a suitable connection to a source of RF voltage and, if necessary, to a source of cooling fluid input and output flow of which are marked by arrows 170 and 172. In operation, the disposable assembly 210 is inserted into guides 246 of hand piece 250. Guides 246 have metalized surfaces through which the required RF voltage (energy) is conveyed to contacts 226 of the disposable assembly 210. When the applicator 250 is applied to a target section of skin 260 to be treated and the operator/caregiver applies the necessary or desired pressure, the wall 218 conforms the skin topography and fluid, filling it provides the positive backpressure enabling tight contact or complete conformance with the target sections of skin being treated. Contact elements or domes 120, as show in FIGS. 7A and 7B are configured to contact the skin and conduct current at a plurality of discrete and separate locations. When the applicator 250 is applied to the skin 260 surface, and RF voltage (energy) is supplied to domes 120, a local electric skin breakdown is generated which produces in the skin, markings similar to the earlier described micro wounds. The electric discharge ablates a plurality of sections of the skin which is in contact with domes 120, and electric current or arc flowing through the opening in the skin micro wounds, thereby causing simultaneous heating of a plurality of skin volumes to a coagulation temperature. The current coagulates the skin at the contact points and the skin volumes which are in the immediate vicinity with the contact points. Upon completion of the patient treatment, assembly 210 may be disposed. Generally, because the applicator 250 comprises mainly a hand piece 254 with suitable connections to a source of voltage and a source of cooling fluid, the whole applicator may be disposed.

Although the electrical discharge breaks down the stratum corneum, the treatment by itself is a non-invasive treatment because the domes do not penetrate the skin. The source of RF voltage may provide a unipolar or bipolar voltage. Depending on the type of the flexible carrier, the electromagnetic energy (RF voltage) may be applied simultaneously to all elements 116 (FIG. 1B) terminated by domes 120, to selected groups of elements 116, or to individual elements 116. The RF voltage (electromagnetic energy) may be applied to elements 116 terminated by domes 120 in a predetermined or random sequence, as well as in a pattern and sequence that minimizes skin heating by, for example, operating every third or fourth row of domes 120. The electromagnetic energy may also be applied to different domes at different power levels.

Figure 8A:
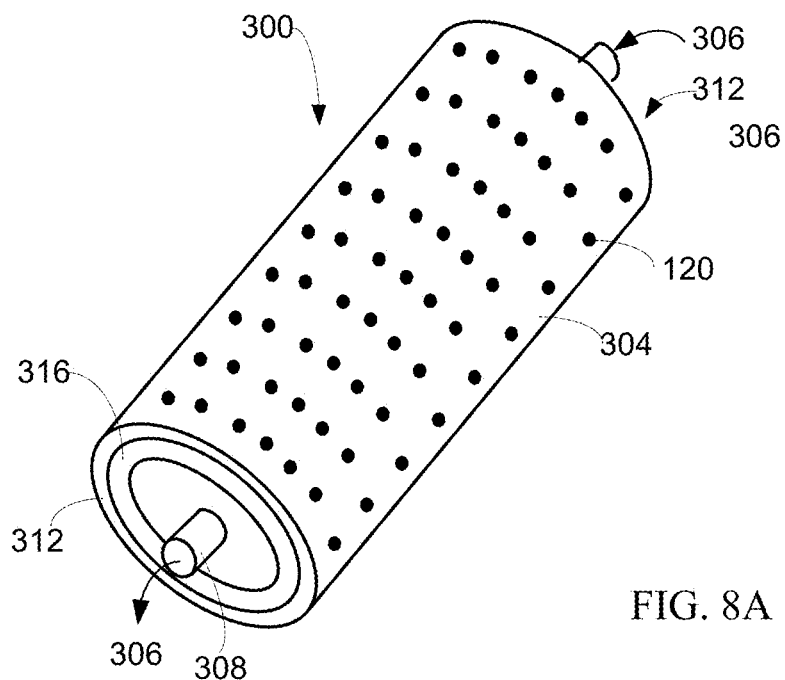
FIGS. 8A and 8B are perspective views illustrating additional exemplary embodiments of disposable flexible voltage-to-skin application elements carriers.
Figure 8B:
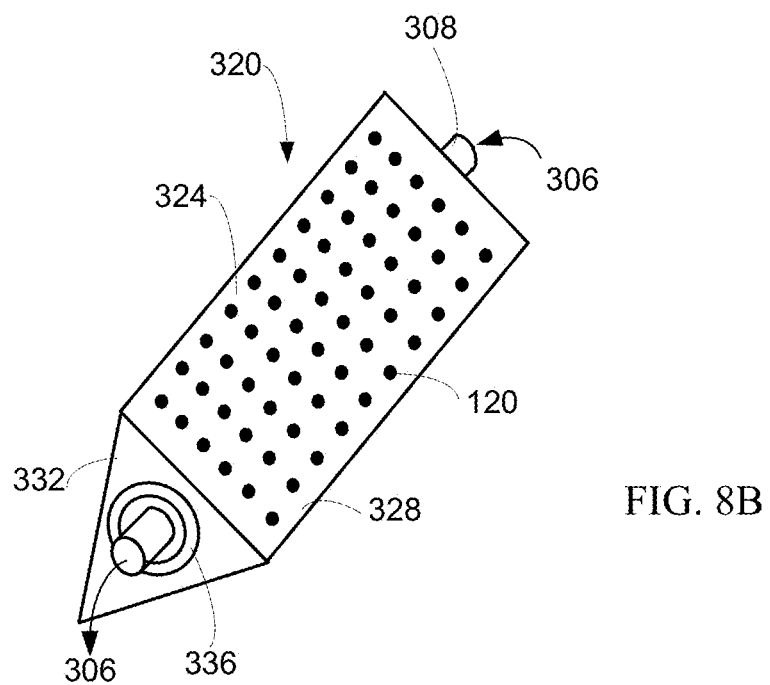

FIGS. 8A and 8B are perspective views illustrating additional exemplary embodiments of disposable flexible voltage-to-skin application elements carriers. FIG. 8A illustrates a three-dimensional carrier 300 having a cylindrical shape. Conductive elements 116 (FIG. 1B) are configured such that domes 120 protrude from external surface 304 of facets 328 of carrier 300. Carrier 300 may be produced by tensioning flexible substrate, similar to substrate 104 over a carcass, which may be a solid cylinder or a squirrel cage type structure. Cooling fluid 306 may be supplied to carrier 300 through a hollow axis 308 on which the carrier 300 rotates. Cooling fluid may flow through the inner section of carrier 300. Sides 312 of carrier 300 may bear contact strips 316 through which the RF voltage can be supplied to domes 120. Such a configuration of the carrier 300 allows it to be applied to a relatively large section of skin. In the context of the present disclosure, "a large section of skin" means a section of skin dimensions of which exceed the dimensions of the surface of the carrier, or circumference of the surface of the contact electrode or electrodes carrier.

Carrier 300 has a rotational symmetry and can be easy repositioned for treatment of a neighboring skin section by rolling it on the skin, providing a reasonable time for thermal relaxation of the earlier treated skin section and returned back to the same earlier treated skin section. The repositioning or rolling of the carrier 300 over the skin is such that the domes 120 remain in permanent contact with the skin and accordingly do not leave sections or patches of the skin that were not treated. Advantageously, this embodiment eliminates the residual patchwork type skin pattern. This type of skin treatment actually represents a continuous skin surface treatment process. The number of disposable parts exchanges and time associated with such exchanges is reduced and use of the applicator is further improved.

FIG. 8B illustrates a three-dimensional carrier 320 having a triangular prism shape. Elements 116 (FIG. 1B) terminated by domes 120 are located such that they protrude from an external surface 324 of facets 328 of carrier 320. Carrier 320 may be produced by tensioning flexible substrate, similar to substrate 104 over a triangular carcass, which may be a solid body or a cage type structure. Alternatively, each of the facets may be made of separate rigid carriers similar to carrier 144. Cooling fluid 306 may be supplied to the inner section of carrier 320 through a hollow axis 308 on which carrier 320 rotates. Sides 332 of carrier 320 may bear contact strips 336 through which voltage can be supplied to elements 116 terminated by domes 120. Such a configuration of the carrier increases its useful life and reduces the time associated with such exchanges of disposable parts. Carrier 320 has a rotational symmetry and can be easy repositioned.

Figure 8C:
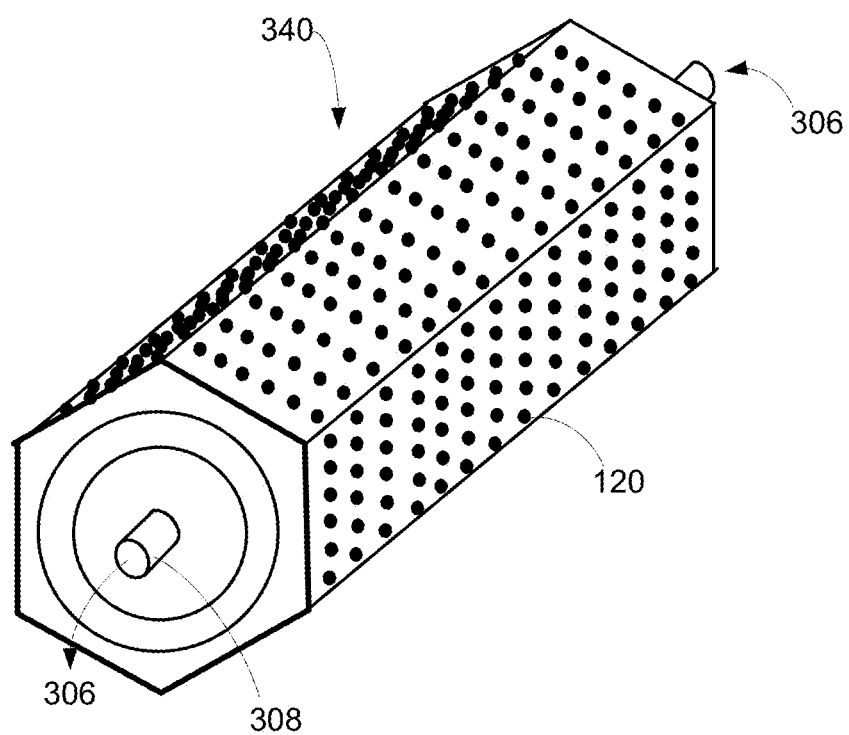
FIG. 8C illustrates a three-dimensional carrier having a hexagonal prism shape.

FIG. 8C illustrates a three-dimensional carrier 340 having a hexagonal prism shape. The structure of carriers 300 and 320 and methods of their manufacture are mutatis mutandis applicable to carrier 340. Generally, any polygonal shape may be used for the carriers similar to carriers 300, 320, and 340. Polygonal shaped carriers have a rotational symmetry and can be easy and continuously repositioned treating a surface area larger than the carrier surface sections of the skin.

Figure 9A:
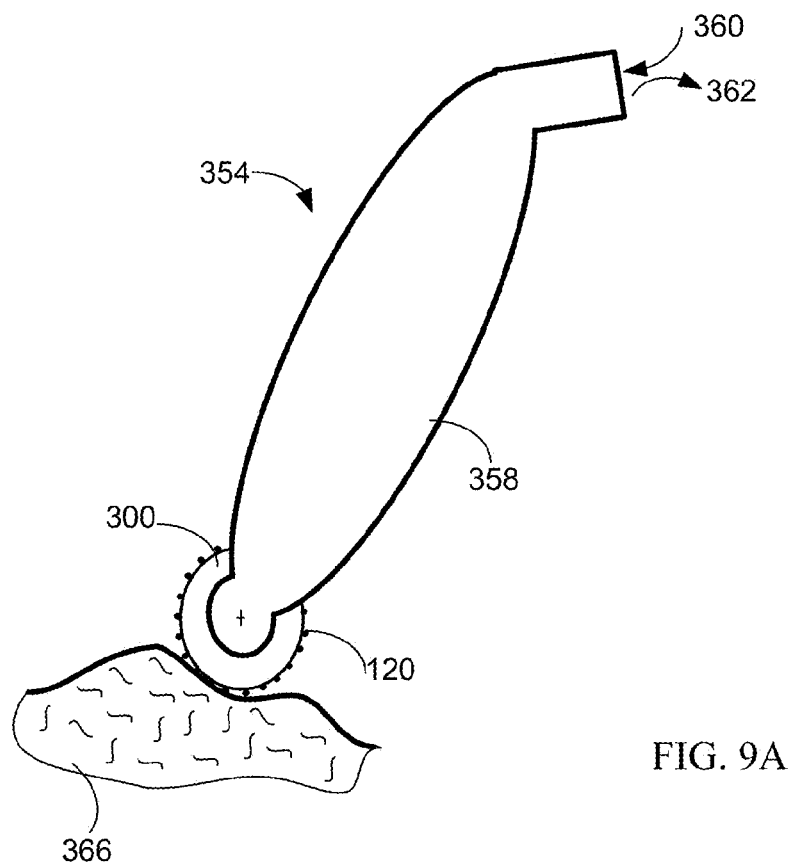
FIGS. 9A and 9B are environmental drawings illustrating the use of the applicators illustrated in FIGS. 8A and 8C.
Figure 9B:
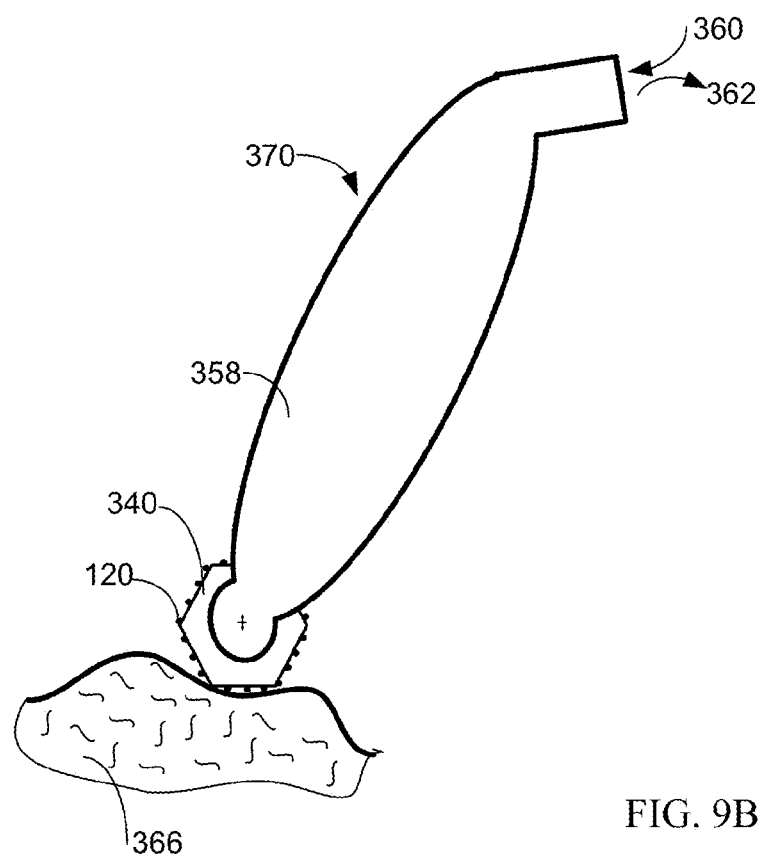

FIGS. 9A and 9B are environmental drawings illustrating the use of the applicators illustrated in FIGS. 8A and 8C. FIG. 9A illustrates an applicator 354 consisting of a handle 358 having connection to a cooling fluid supply. Arrows 360 and 362 schematically illustrate the flow of cooling fluid into and out of applicator 354 and further into carrier 300. Carrier 300, as explained above, is in permanent contact with skin 366. The treated surface is affected by rolling the carrier over the skin. FIG. 9B illustrates an applicator 370 utilizing the disposable carrier 340 of FIG. 8C.

Figure 10A:
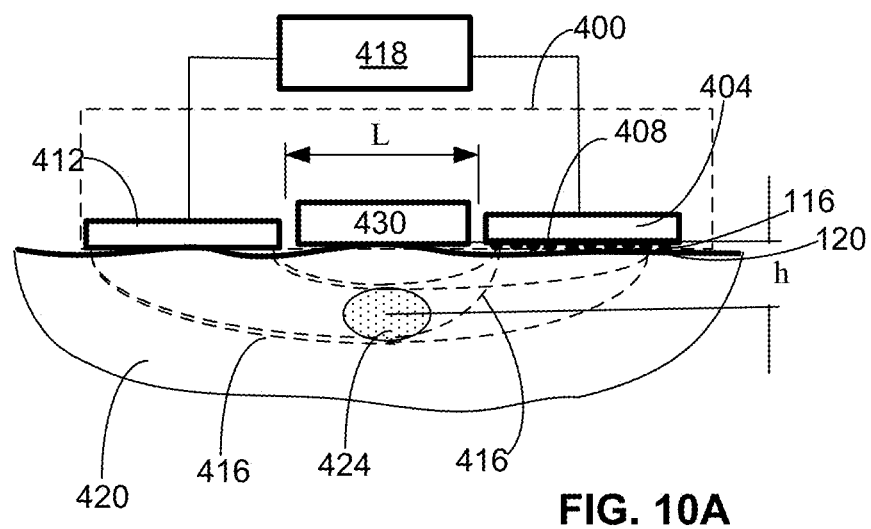
FIGS. 10A and 10B illustrate yet another exemplary embodiment of an applicator employing a disposable rigid and flexible voltage-to-skin application elements carrier.
Figure 10B:
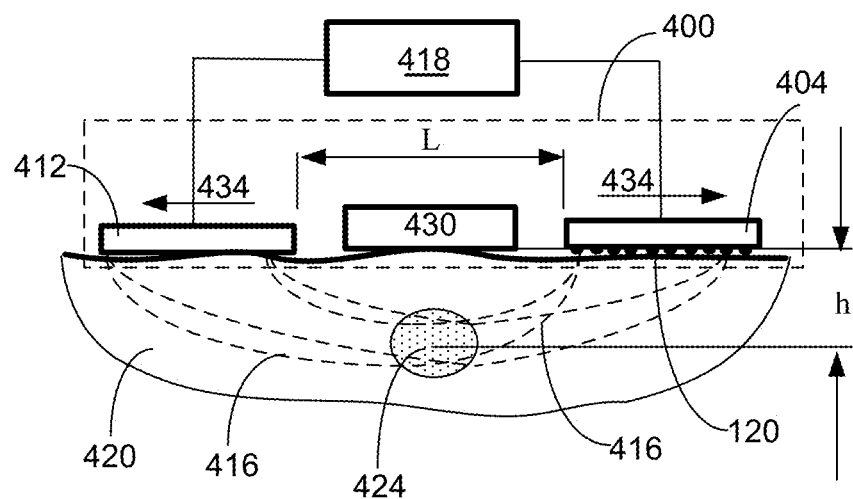

FIGS. 10A and 10B illustrate yet another exemplary embodiment of an applicator employing a disposable rigid and flexible voltage-to-skin application elements carrier. Applicator 400 (FIG. 10A) includes a carrier 404 populated by voltage-to-skin conductive elements 116 configured such that domes 120 terminating elements 116 protrude from an external surface 408 of carrier 404. The opposite electrode 412 is a conventional flat rigid or flexible electrode. In the current disclosure, the term "conventional electrode" means an electrode with one continuous conducting surface. Phantom lines 416 schematically illustrate the induced electric current flow lines provided by a source of RF voltage 418. Practically, the current flows through skin 420 from each dome 120 in a diverging manner communicating with almost the entire electrode 412 surface. Volume 424 represents a treated volume through which current generated by all of the domes 120 flows. This current heats volume 424 and shrinks or destroys collagen. As noticed earlier, carrier 404 enables addressing of all elements 116 (not shown) terminated by domes 120, a group of elements 116, or each of the elements 116 individually. By operating a proper amount of elements 116 and varying or changing their operation sequence, it is possible to vary the current and its effects on the common volume of tissue 424. For example, by randomly operating different elements 116 it is possible to generate a uniform or homogenous skin heating pattern and avoid formation of hot spots. It is also possible to adapt the treatment parameters, such as pulse frequency, temperature, order of different domes operation etc. to the needs of a particular patient.

A cooling arrangement 430 of any known type may be used to cool skin 420 and in particular volume 424. By varying the rate at which heat is evacuated from the treatment volume, it is possible to affect further the treatment parameters of volume 424. This may be done by varying the temperature of the cooling fluid or the flow rate of the fluid.

FIG. 10B shows a method of variation of the treatment volume 424 location within the skin and in particular, the depth "h" at which volume 424 is located. Carrier 404 and conventional electrode 412 may be moved by any known mechanism, as shown by arrows 434 towards or away from each other. Change of the distance L between carrier 404 and electrode 412 changes the depth h of treated volume 424 location within the depth of skin, thereby providing an additional parameter for treatment to patient needs adaptation and individualization. In these embodiments, the relationship between the surfaces of the voltage-to-skin application elements being in contact with the skin to the surface of the electrode being in contact with said skin is greater than at least 1 to 1,000,000.

Figure 11A:
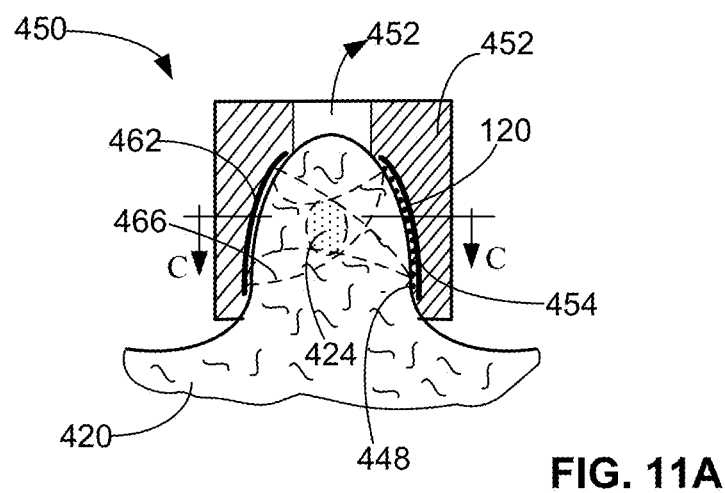
FIGS. 11A and 11B illustrate another exemplary embodiment of an applicator employing a disposable rigid and flexible voltage to skin application elements carrier.
Figure 11B:
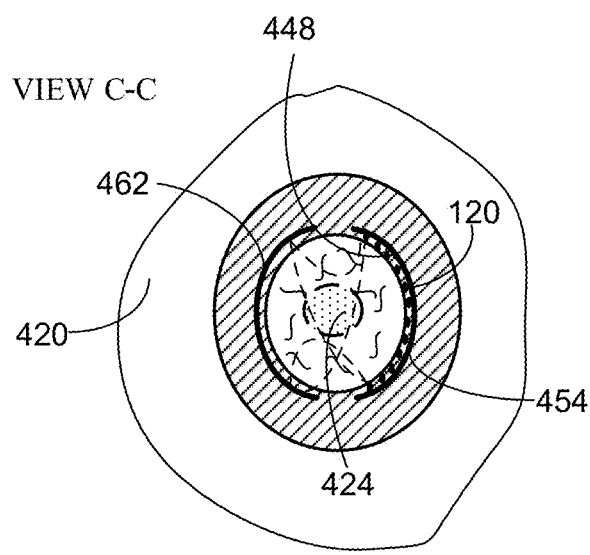

FIGS. 11A and 11B illustrate another exemplary embodiment of an applicator employing a disposable rigid and flexible voltage to skin application elements carrier. Applicator 450, as shown in FIGS. 11A and 11B is of a cylindrical shape, although it can also be other shapes, such as linear or polygonal shape. Applicator 450 (FIG. 11A) includes a flexible carrier 454 populated by conductive elements 116 (FIG. 1B) configured such that domes 120 protrude from the surface 448 of carrier 454. Surface 448 is oriented towards the target section of the skin to be treated. The opposite electrode 462 is a conventional flat rigid or flexible electrode, or an electrode representing a segment of a cylindrical surface oriented parallel to the skin. Phantom lines 466 schematically illustrate the induced electric current flow lines provided by a source of RF (not shown). Applicator 450 is connected to a source of vacuum that when operated, pulls-in, as shown by arrow 452, a section of skin 420, such that it creates a protrusion and forms good contact with domes 120 of carrier 454 and conventional electrode 462. When RF voltage is applied to carrier 454 and conventional electrode 462, the generated current flows in a diverging manner through skin 420 from each dome 120 communicating with almost the entire electrode 462 surface. Volume 424 represents a volume through which current generated by all and each of domes 120 flows. Similar to the embodiments of FIGS. 8A and 8B, carrier 454 enables addressing of all domes 120, including addressing of individual domes 120. By operating a proper amount of domes 120, it is possible to vary the magnitude of the current and its effects on the common volume of tissue 424. It is also possible to adapt the treatment parameters to the needs of a particular patient. Additional treatment parameters variation may be enabled by introduction of skin/tissue cooling. As the outer part of the skin cools, the electrical resistance of it grows and the current flows through deeper and hotter having lower resistance skin layers. By randomly switching which of domes 120 are participating in the process, it is possible to create a uniform current flow through the skin and avoid hot spots on electrode 462.

Figure 12:
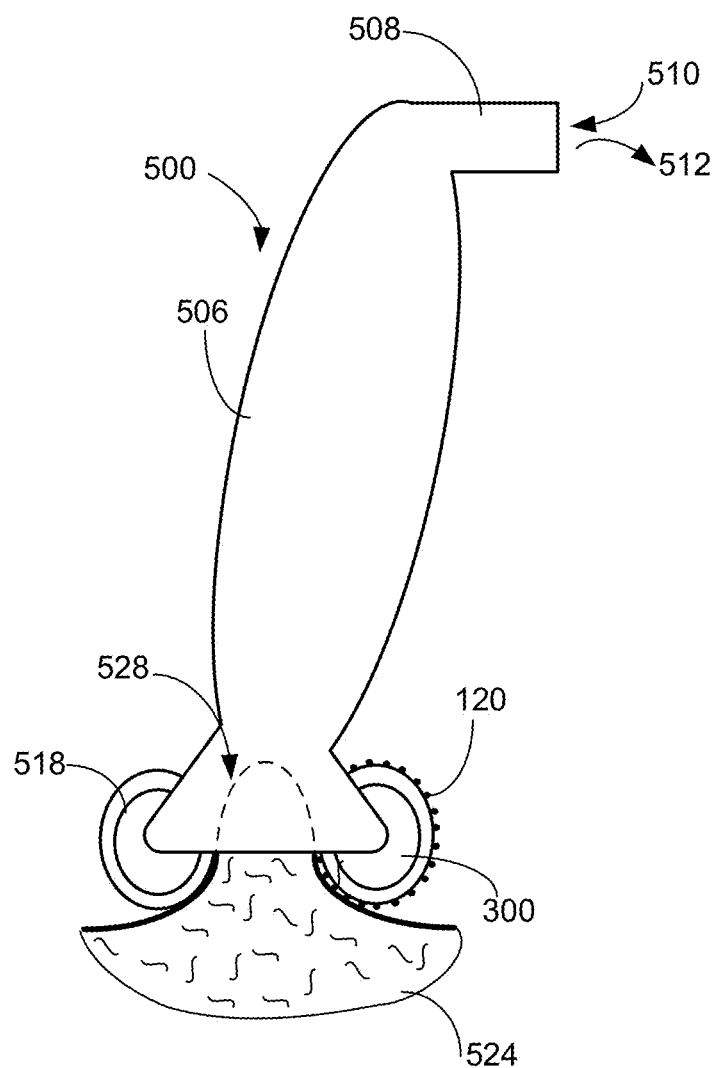
FIG. 12 is a schematic illustration of another exemplary embodiment of an applicator with carriers of FIG. 8A and conventional electrodes configured as three-dimensional bodies.

FIG. 12 is a schematic illustration of another exemplary embodiment of an applicator with carriers of FIG. 8A and conventional electrodes configured as three-dimensional bodies. Applicator 500 consists of a handle 506 having a connection to cooling fluid supply 508. Arrows 510 and 512 schematically illustrate the flow of cooling fluid into and out of applicator 500 and further into carrier 300 and conventional electrode 518 configured as a hollow cylinder. Electrode 518 may be made of metal or plastic having its external surface metal coated. Cooling fluid supply is configured such that the cooling fluid passes inside carrier 300 and electrode 518 cooling sections of skin 524 being in contact with them.

Applicator 500 is applied to the skin surface 524 and forms a skin protrusion 528. Skin protrusion 528 may be generated by suction or mechanical means. It is known for example, to generate a skin protrusion by applying to skin simultaneously two rollers, such as carrier 300 and electrode 518, and rotating them with different speed or in opposite direction. By applying an RF voltage to carrier 300 and electrode 518 it is possible to generate current that flows through skin 524 from each dome 120 being in contact with skin to corresponding sections of electrode 518 in a manner similar to one described in relation to FIGS. 10A and 10B. By regulating the height of protrusion 528 and operating a proper amount of domes 120 it is possible to regulate the treated skin (tissue) volume and adapt the treatment parameters to each individual patient needs. Additional adaptations of the treatment parameters to patient needs are possible by changing the temperature of the skin/cooling fluid and speed of applicator 500 advance.

While the exemplary embodiment of the present method and apparatus has been illustrated and described, it will be appreciated that various changes can be made therein without affecting the spirit and scope of the apparatus and method. The scope of the method, therefore, is defined by reference to the following claims:

In the description and claims of the present application, each of the verbs, "comprise", "include" and "have", and conjugates thereof, are used to indicate that the object or objects of the verb are not necessarily a complete listing of members, components, elements, or parts of the subject or subjects of the verb.

The present apparatus and method have been described using detailed descriptions of embodiments thereof that are provided by way of example and are not intended to limit the scope of the invention. The described embodiments comprise different features, not all of which are required in all embodiments of the apparatus. Some embodiments of the present apparatus and method utilize only some of the features or possible combinations of the features. Variations of embodiments of the present apparatus that are described and embodiments of the present method comprising different combinations of features noted in the described embodiments will occur to persons of the art.

It will be appreciated by persons skilled in the art that the present invention is not limited by what has been particularly shown and described herein above. Rather the scope of the invention is defined by the claims that follow.

What is claimed is:

1. A three-dimensional carrier for use in conjunction with a skin treatment apparatus, said carrier comprising:
   a rotational symmetry body formed by tensioning a flexible substrate over a squirrel cage type carcass rotating on a hollow axis;
   an array of miniature, discrete conductive elements located on an external surface of the flexible substrate tensioned over a squirrel type carcass said miniature conductive elements configured to provide a conductive path to skin surface contacting at a least a portion of said array; and
   an inner section of the three dimensional carrier configured to contain a cooling fluid supplied through the hollow axis of the three dimensional carrier; and
   wherein the cooling fluid is supplied to cool the skin surface contacting at least a portion of the array of discrete conductive elements.

2. The three-dimensional carrier according to claim 1, wherein the substrate is made of insulating material and wherein the insulating material is a polyimide film having a thickness ranging from about 12.5 micron to about 150 micron.

3. The three-dimensional carrier according to claim 1, further comprising a plurality of electric conductors deposited on the inner side of the substrate and configured to provide RF energy to each individual conductive element.

4. The three-dimensional carrier according to claim 3, wherein the plurality of electric conductors located on the inner side of the substrate interfaces the plurality of the electric conductors with a source of RF voltage.

5. The three-dimensional carrier according to claim 1, wherein the array of miniature, discrete conductive elements located on the external surface of the flexible substrate is one of a group consisting of evenly or randomly spaced matrix discrete conductive elements.

6. The three-dimensional carrier according to claim 1, wherein the three-dimensional carrier is one of a group of carriers consisting of a cylindrically shaped carrier and a polygonal shaped carrier.

7. The three-dimensional carrier according to claim 1, wherein RF energy provided to the array of miniature discrete conductive elements is sufficient to cause an electrical discharge and break down stratum corneum.

8. The three-dimensional carrier according to claim 1, wherein RF energy provided to each element of the array of miniature discrete conductive elements is applied to a selected groups of elements, to all elements, or to each individual element.

* * * * *